(12) United States Patent
Juryozawa et al.

(10) Patent No.: US 6,709,629 B2
(45) Date of Patent: Mar. 23, 2004

(54) VACUUM HEAT TREATMENT FURNACE

(75) Inventors: Hidetoshi Juryozawa, Tokyo (JP);
Keiji Yokose, Tokyo (JP); Fumitaka Abukawa, Tokyo (JP); Jun Takahashi, Tokyo (JP); Hisashi Ebihara, Tokyo (JP)

(73) Assignee: Dowa Mining Co., Ltd., Tokyo (JP)

( * ) Notice: Subject to any disclaimer, the term of this patent is extended or adjusted under 35 U.S.C. 154(b) by 0 days.

(21) Appl. No.: 10/108,770

(22) Filed: Mar. 28, 2002

(65) Prior Publication Data

US 2002/0189322 A1 Dec. 19, 2002

(30) Foreign Application Priority Data

Jun. 4, 2001 (JP) ........................... 2001-168471
Jun. 4, 2001 (JP) ........................... 2001-168472

(51) Int. Cl.$^7$ ................................. C21D 1/62
(52) U.S. Cl. .......................... 266/130; 266/130
(58) Field of Search ................. 266/130, 252; 65/424; 524/442

(56) References Cited

U.S. PATENT DOCUMENTS

| | | | |
|---|---|---|---|
| 2,698,222 A | 12/1954 | Davis, II | 23/232 |
| 3,817,084 A | 6/1974 | Whitehead | 73/15 |
| 4,118,016 A * | 10/1978 | Westeren et al. | 266/130 |
| 5,643,987 A * | 7/1997 | Dismukes et al. | 524/442 |
| 5,713,979 A * | 2/1998 | Nicholson et al. | 65/424 |
| 2003/0020214 A1 * | 1/2003 | Poor et al. | 266/252 |

FOREIGN PATENT DOCUMENTS

| | | | |
|---|---|---|---|
| EP | 0 191 973 | 8/1986 | |
| JP | 04103801 | * 4/1922 | ........... C04B/35/52 |
| JP | 35411/1970 | 11/1970 | |
| JP | 46397/1991 | 11/1992 | |

OTHER PUBLICATIONS

JP 2001 012861 Abstract, Database WPI, Section Ch, Week 200123, XP–02211102, Derwent Publications Ltd.

* cited by examiner

*Primary Examiner*—Hezron Williams
*Assistant Examiner*—Jay Politzer
(74) *Attorney, Agent, or Firm*—Patterson, Thuente, Skaar & Christensen, P.A.

(57) ABSTRACT

A vacuum heat treatment furnace comprising a furnace shell, a casing arranged in an inner side of the furnace shell, a heat insulating layer consisting of a thick plate-like alumina-silica series ceramic fiber blanket and a thin plate-like alumina series ceramic material arranged in an inside of the casing, and a heater arranged in a heating room surrounded by the heat insulating layer. A method of and apparatus for measuring a carbon concentration in an atmosphere in a treating room having a reduced pressure, wherein a carbon concentration measuring body is transferred from an external portion of a furnace shell of a heat treatment furnace into the treating room within the furnace shell, the carbon concentration measuring body is reacted with the atmosphere in the treating room for a predetermined time, the carbon concentration measuring body is gradually cooled for a predetermined time, and an amount of carbon in the carbon concentration measuring body is measured in the atmospheric pressure at a room temperature.

8 Claims, 9 Drawing Sheets

UNDER VACUUM (2Pa)

FIG. 2B

UNDER N2 ATMOSPHERE (0.1 MPa)

FIG. 3A

UNDER VACUUM (0.4Pa)

FIG. 3B

UNDER N2 ATMOSPHERE (0.1MPa)

VACUUM HEAT TREATMENT FURNACE

BACKGROUND OF THE INVENTION

1. Field of the Invention

The present invention relates to a vacuum heat treatment furnace, and more particularly to a vacuum heat treatment furnace structured such as to prevent a deterioration due to a carburizing and increase an efficiency of thermal energy with respect to a subject or a work to be treated in a vacuum heat treatment, a vacuum carburizing treatment and the like, and a method of and apparatus for measuring a carbon concentration in an atmosphere having a reduced pressure.

2. Description of the Prior Art

A method of carburizing an iron and steel material under a reduced pressure conventionally includes a vacuum carburizing method carried out by introducing a hydrocarbon series gas within a furnace, in which a carbon material is frequently employed for a heat insulating material and a heater as furnace constituting members, and a heat resisting steel, a heat resisting cast steel, a carbon series material or the like is employed for a hearth rail for supporting the subject to be treated and a hearth roller for transferring. Further, the vacuum heat treatment furnace has a type in which a furnace wall is water cooled and a type in which the furnace wall is not water cooled by making the heat insulating material thick so as to increase a heat insulating property, in view of a working environment and the heat insulating property.

However, in the case that the iron series material (a hard carburized material: containing a high Ni high Cr material) is used for the furnace constituting material in a high temperature range, the furnace constituting material is also carburized at the same time when the subject to be treated is carburized, in the vacuum carburizing treatment, so that there is a case that the material becomes brittle and is broken. Further, even in the case of making the heat insulating material thick without water cooling the furnace wall so as to increase the heat insulating property and reduce an amount of heat radiation, for the purpose of reducing the thermal energy, a large amount of heat reserve of the heat insulating material is required, so that the thermal energy required for increasing the temperature is increased and a lot of time is also required for reducing the temperature.

Further, as a means for directly measuring a carburizing within a heat treatment furnace or a carbon concentration of an anti-oxidized atmosphere, a steel wire method is shown, for example, in Japanese Patent Publication No. 45-35411. Further, with respect to a holding rod for holding the steel wire for measuring the carbon concentration, for example, there is a structure shown in Japanese Utility Model No. 2586972.

However, the measurement in accordance with the steel wire method is carried out by inserting the steel wire for measuring the carbon concentration into an atmosphere normally equal to or more than an atmospheric pressure, and it is hard to insert the steel wire for measuring the carbon concentration in the atmosphere having the reduced pressure. Further, the vacuum carburizing under the reduced pressure corresponds to a treatment in which a carbon is directly carburized into the steel, and it is not carried out to control and measure the carbon concentration in the atmosphere within the furnace.

SUMMARY OF THE INVENTION

The present invention solves the problems mentioned above.

An object of the present invention is to provide a vacuum heat treatment furnace comprising a furnace shell, a casing arranged in an inner side of the furnace shell, a heat insulating layer consisting of a thick plate-like alumina-silica series ceramic fiber blanket and a thin plate-like alumina series ceramic material arranged in an inside of the casing, and a heater arranged in a heating room surrounded by the heat insulating layer.

Another object of the present invention is to provide a vacuum heat treatment furnace comprising a furnace shell, a casing arranged in an inner side of the furnace shell, a heat insulating layer consisting of a thick plate-like alumina-silica series ceramic fiber blanket of multilayer and a thin plate-like alumina series ceramic material arranged in an inside of the casing, and a heater arranged in a heating room surrounded by the heat insulating layer.

A further object of the present invention is to provide the vacuum heat treatment furnace, wherein at least one layer in the ceramic fiber blanket of multilayer consists of a board, felt or plate of carbon fiber.

Still further object of the present invention is to provide the vacuum heat treatment furnace, further comprises a fan formed of a high strength carbon fiber for circulating by convection gas atmosphere, arranged in the heating room surrounded by the heat insulating layer.

Yet further object of the present invention is to provide the vacuum heat treatment furnace, further comprises a roller for transferring a subject to be treated, and a tray guide which is easy to replace and prevents the surface of the roller from being damaged, both of the roller and the tray guide being arranged in the heating room surrounded by the heat insulating layer.

Yet still further object of the present invention is to provide the vacuum heat treatment furnace, further comprises a work position detecting flapper arranged in the heating room surrounded by the heat insulating layer.

A further object of the present invention is to provide an apparatus for measuring a carbon concentration in an atmosphere having a reduced pressure comprising a carbon concentration measuring body insertion port communicating between an external portion of a furnace shell of a heat treatment furnace and a treating room within the furnace shell, means for exhausting an internal portion of the port, means for maintaining a vacuum seal of a portion of the port outside of the furnace shell, means for transferring a carbon concentration measuring body from the external portion of the furnace shell into the treating room, and means for measuring an amount of carbon in the carbon concentration measuring body.

Yet further object of the present invention is to provide the apparatus for measuring a carbon concentration, wherein means for maintaining the vacuum seal of the portion of the port outside of the furnace shell is means for fastening and holding the carbon concentration measuring body transferring means.

Still further object of the present invention is to provide a method of measuring a carbon concentration in an atmosphere having a reduced pressure comprising the steps of exhausting an internal portion of a carbon concentration measuring body insertion port communicating between an external portion of a furnace shell of a heat treatment furnace and a treating room within the furnace shell, transferring a carbon concentration measuring body from a portion of the port outside of the furnace shell into the treating room, reacting the carbon concentration measuring body with the atmosphere in the treating room for a predetermined time, gradually cooling the carbon concentration measuring body for a predetermined time, drawing out the carbon concentration measuring body to the portion of the port outside of the furnace shell, cooling the carbon concentration measuring body to a room temperature, and measuring an amount of carbon in the carbon concentration measuring body in the atmospheric pressure.

Yet still further object of the present invention is to provide the apparatus for measuring a carbon concentration, wherein the carbon concentration measuring body is a carbon concentration measuring steel wire, a carbon concentration measuring steel foil or a test piece of a subject to be carburized.

The forgoing and other objects, features, and advantages of the present invention will become apparent from the following more particular description of preferred embodiments of the invention, as illustrated in the accompanying drawings.

DESCRIPTION OF THE PREFERRED EMBODIMENT

Figure 1:
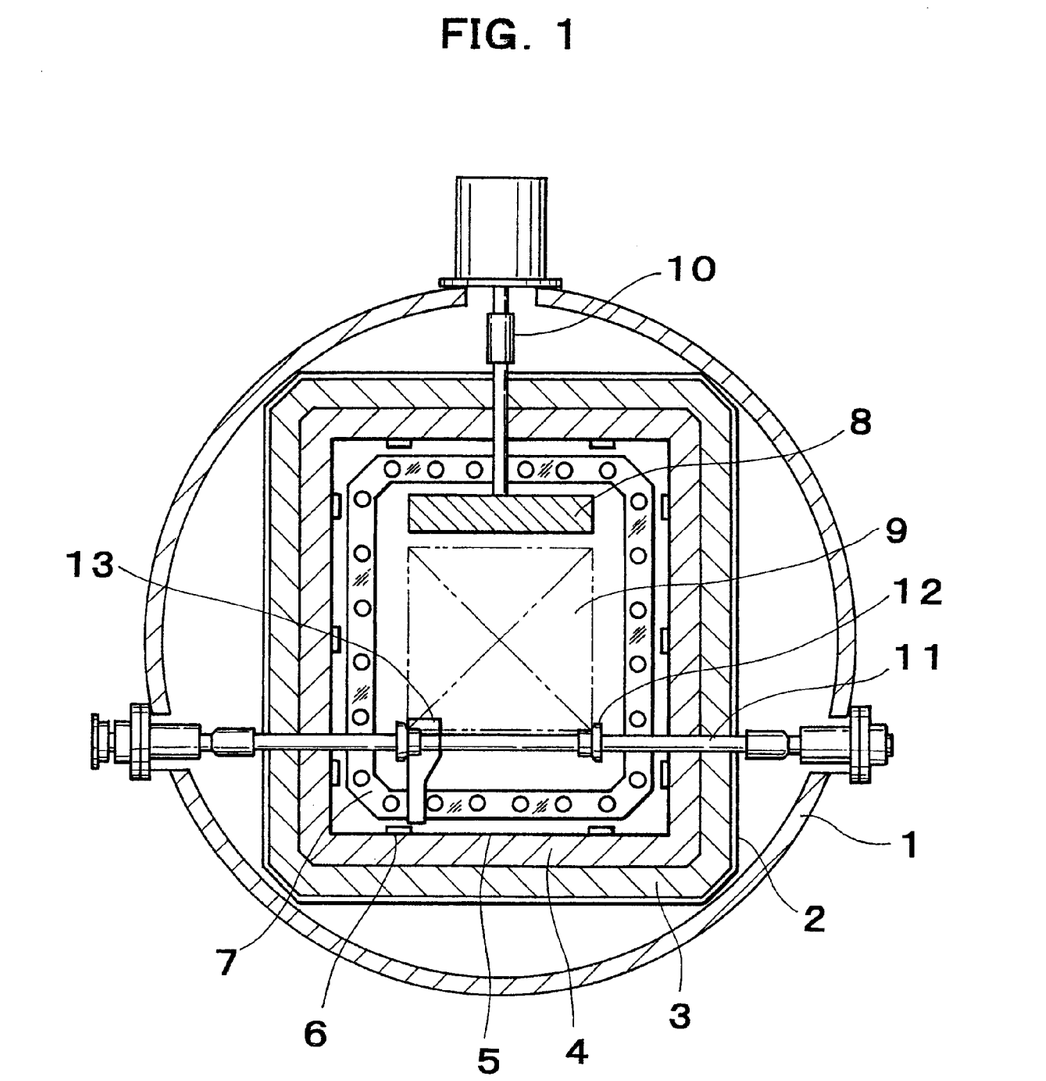
FIG. 1 is a vertically sectional front view of a vacuum heat treatment furnace according to the present invention.

As shown in FIG. 1, a vacuum heat treatment furnace in accordance with the present invention has a furnace shell 1 of a water-cooled double wall structure and a casing 2 formed of a SUS steel material, a metal net or a punching metal. A heat insulating layer arranged in an inner side of the furnace shell 1 consists of an alumina-silica series ceramic fiber blanket 3 having a thickness of 50 mm, a high alumina-silica series ceramic fiber blanket 4 having a thickness of 50 mm, and a thin plate-like alumina series ceramic compound material 5 having a thickness of 1 mm. They are integrally fixed by ceramic washers and bolts 6 on an inner side of the furnace shell 1.

In place of or in addition to the heat insulating layer comprising the ceramic fiber blankets 3 and 4, and the thin plate-like ceramic compound material 5, a ceramic fiber board, a carbon fiber of a board, felt or plate may be used, in a material cost and some heat insulating material properties to be targeted.

A carbon heater 7 having four surfaces is arranged at an inner side of the heat insulating layer so as to constitute a heating chamber. A light fan 8 formed of a high strength carbon fiber is arranged in an upper portion within the heating chamber, thereby reducing a temperature difference within a subject to be treated 9 arranged within the heating chamber and efficiently conducting the heat by circulating by convection an N2 gas or an inert gas atmosphere to be introduced at a time of increasing or reducing a temperature of the subject to be treated 9 arranged within the heating chamber. A drive shaft of the fan 8 has a small cross section and has a small heat loss caused by the heat conduction, and a connecting portion 10 with respect to the drive shaft is arranged in a space between the furnace shell 1 and the casing 2, whereby it becomes easy to replace the fan 8 and carry out a maintenance by attaching and detaching a pin and a bolt.

A roller 11 formed of a high strength carbon fiber is arranged in a lower portion within the heating chamber so as to pass through an inner portion of an effective heating band range, thereby making it possible to transfer the subject to be treated 9, reduce and increase the temperature of the subject to be treated 9. The roller 11 is light and has a small cross section and a small heat loss. A connecting portion connecting the drive shaft of the roller 11 to a drive source is arranged in the space between the furnace shell 1 and the casing 2, so that the roller can easily be attached and detached, and the replacement and the maintenance of the roller can be carried out easily. In this case, at a time of the transfer motion using the roller 11, since a peel off or a scraping easily occurs in the roller 11 in some carbon fiber directions of the roller contact surface at a time when the subject to be treated 9 moves over the roller 11, a tray guide 12 is put over the roller 11 and the tray guide 12 is exposed to the damage, whereby it is sufficient to replace only the tray guide 12 without damaging the roller 11 itself, so that it becomes economical. The high strength carbon fiber is employed for the tray guide 12, however, a carbon fiber impregnated with Si, a carbon material, a ceramic and the like may be employed. Further, a work position detecting device 13 formed of the high strength carbon fiber is provided within the heating chamber.

Since the iron series material which is in danger of being deteriorated or damaged by the vacuum carburizing treatment is not used within the heating chamber, a maximum heating temperature can be 1473 K. The vacuum heat treatment furnace in accordance with the present invention can be applied to both of a batch type furnace and a continuous furnace.

(Embodiment 1)

A temperature distribution within an effective size within the furnace of the vacuum heat treatment furnace in accordance with the present invention is measured.

Effective size within furnace: length 600 mm, width 300 mm, height 300 mm

Measuring condition: vacuum (2 Pa), empty furnace T/C, nine points for measurement Result: 1123 K . . . temperature width 4.6 K, 1203 K . . . temperature width 4.2 K, 1323 K . . . temperature width 4.5 K As mentioned above, in accordance with the vacuum heat treatment furnace of the present invention, it is possible to achieve a temperature distribution within the temperature width 5.0 K in any temperatures.

(Embodiment 2)

In a temperature increasing and reducing experiment under a vacuum and an N2 gas atmosphere with using the vacuum heat treatment furnace in accordance with the present invention, the temperature difference within the subject to be treated and a temperature increasing and reducing time are compared.

Effective size within furnace: length 600 mm, width 300 mm, height 300 mm

Measuring condition: temperature increasing property, the temperature is increased after inserting the subject to be treated within the furnace having the temperature 1223 K.

Vacuum (2 Pa), N2 gas atmosphere (0.1 MPa), subject to be treated 80 kg by the gross, T/C, five points for measurement Temperature reducing property, the temperature of the subject to be treated kept at the temperature 1223 K is reduced to 1103 K.

Figure 2A:
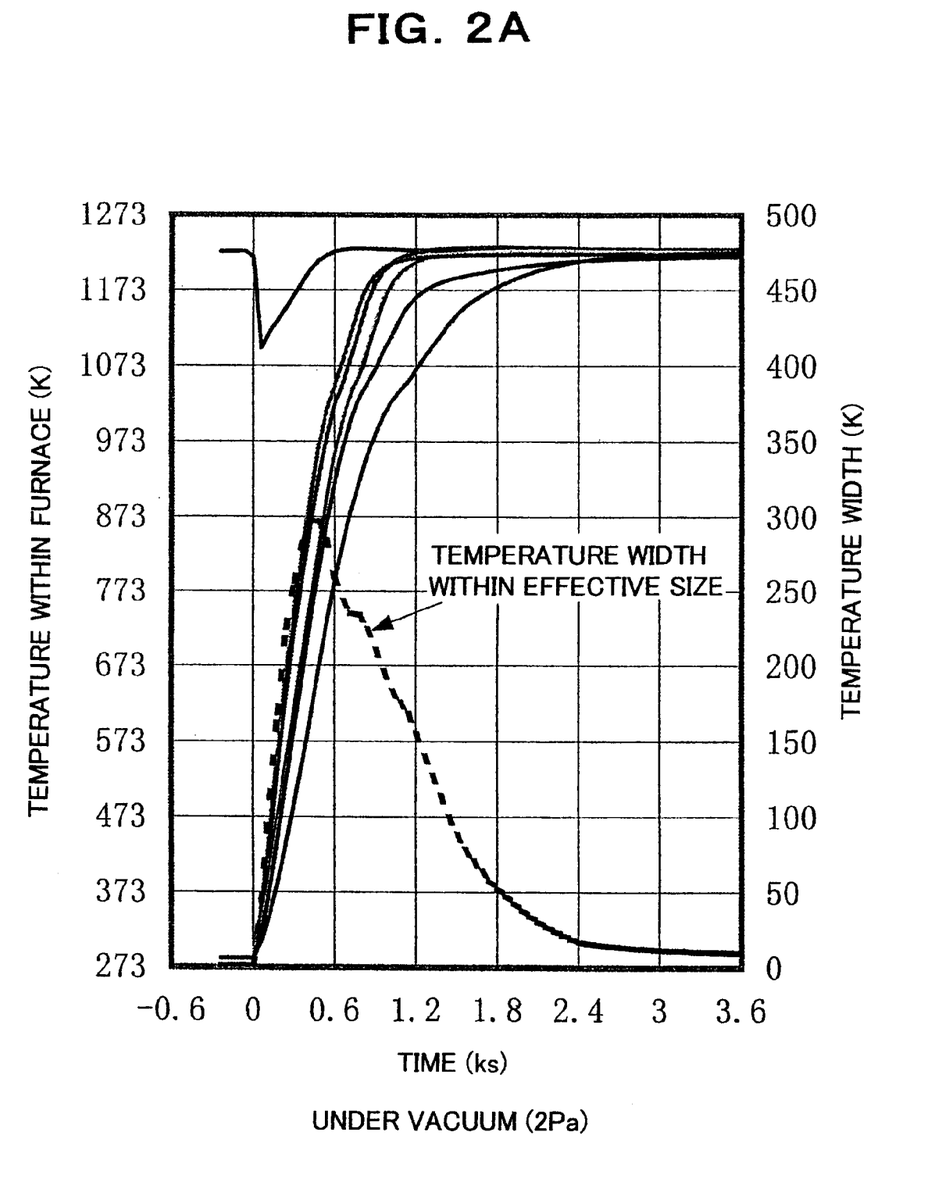
FIG. 2A is a graph showing properties of the vacuum heat treatment furnace shown in FIG. 1 when the temperature is increased in an atmosphere of reduced pressure.

Vacuum (0.4 Pa), N2 gas atmosphere (0.1 MPa), subject to be treated 80 kg by the gross, T/C, nine points for measurement Result: temperature increasing property Under vacuum (2 Pa) . . . maximum temperature width 298 K, time reaching the temperature width 10 K within the subject to be treated 3.4 Ks (shown in FIG. 2A)

Figure 2B:
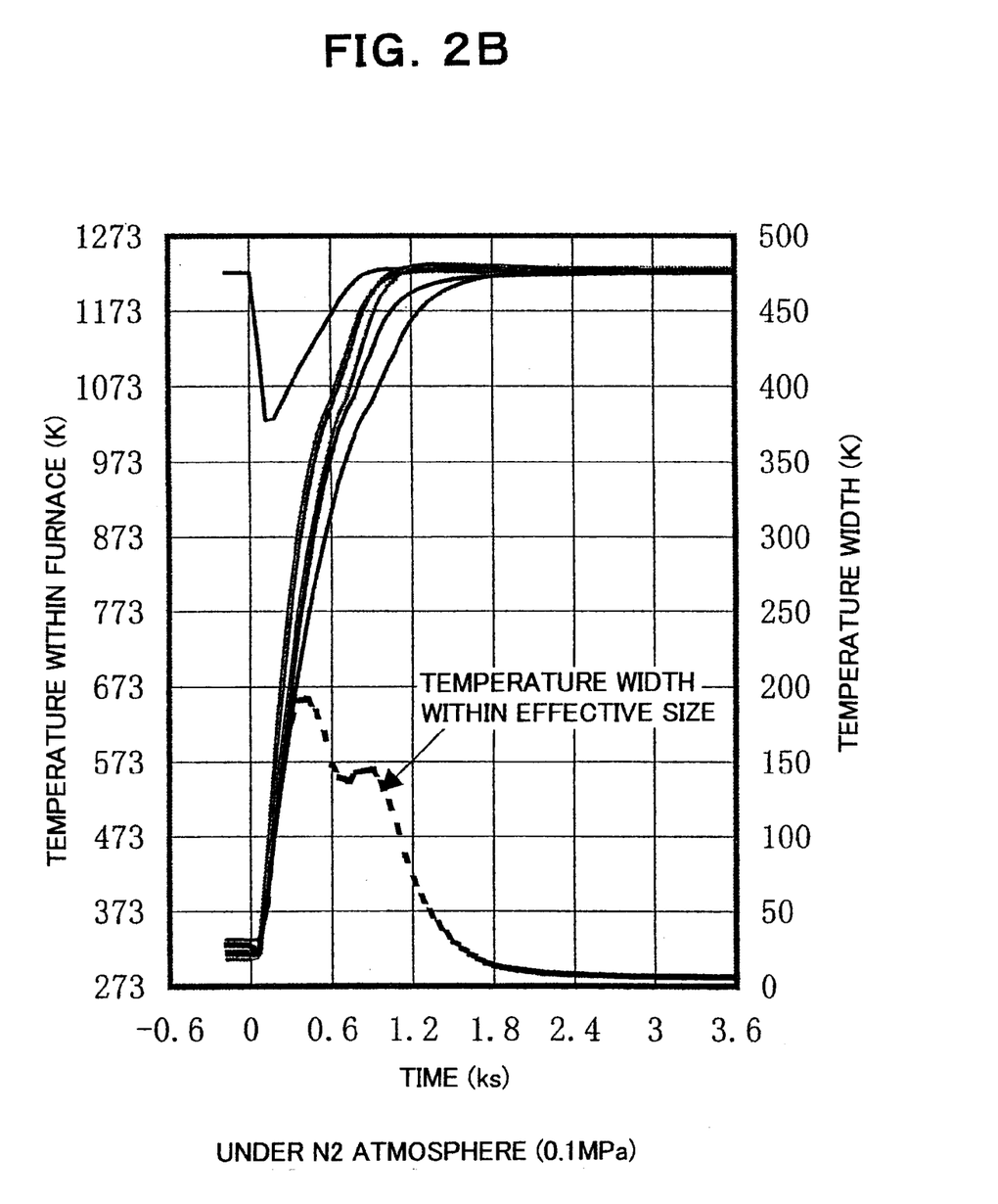
FIG. 2B is a graph showing properties of the vacuum heat treatment furnace shown in FIG. 1 when the temperature is increased in an atmosphere of $N_2$ gas.

Under N2 gas atmosphere (0.1 MPa) . . . maximum temperature width 192 K, time reaching the temperature width 10 K within the subject to be treated 2.0 Ks (shown in FIG. 2B)

Result: temperature reducing property

Figure 3A:
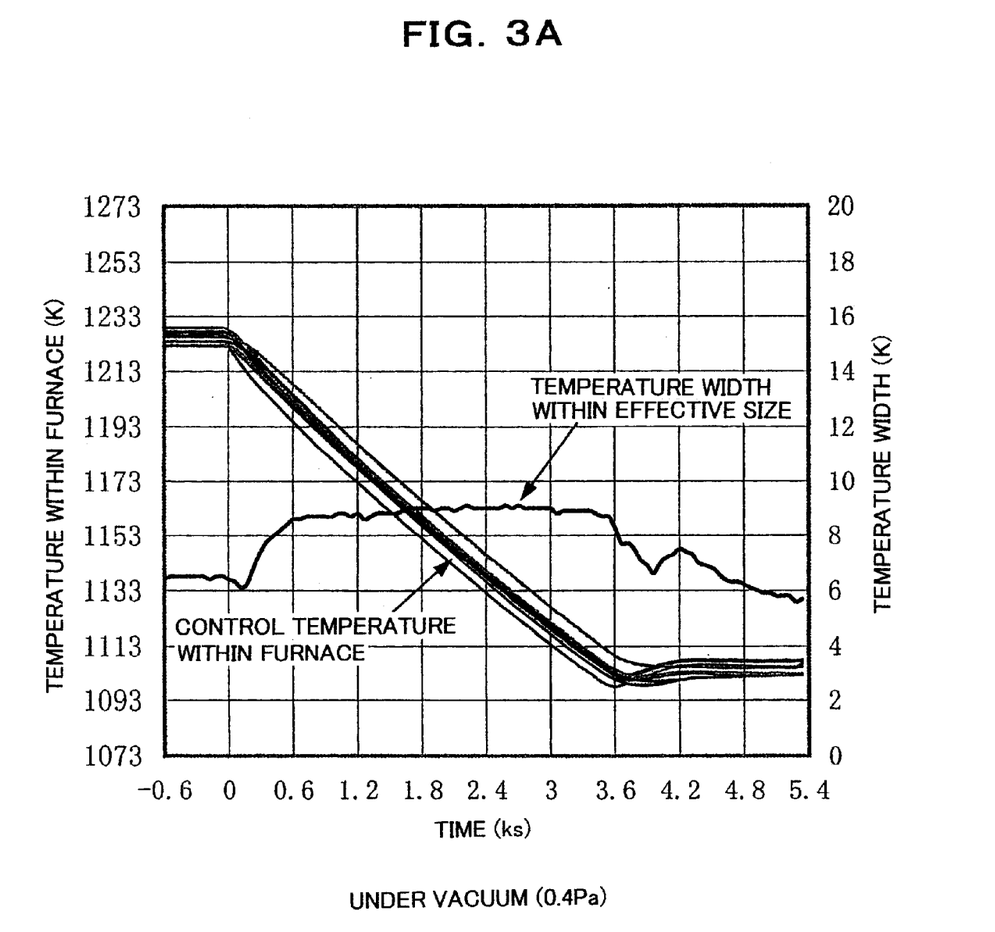
FIG. 3A is a graph showing properties of the vacuum heat treatment furnace shown in FIG. 1 when the temperature is decreased in an atmosphere of reduced pressure.

Under vacuum (0.4 Pa) . . . maximum temperature width 9 K, time reaching the temperature width 1103 K within the subject to be treated 3.7 Ks (shown in FIG. 3A)

Figure 3B:
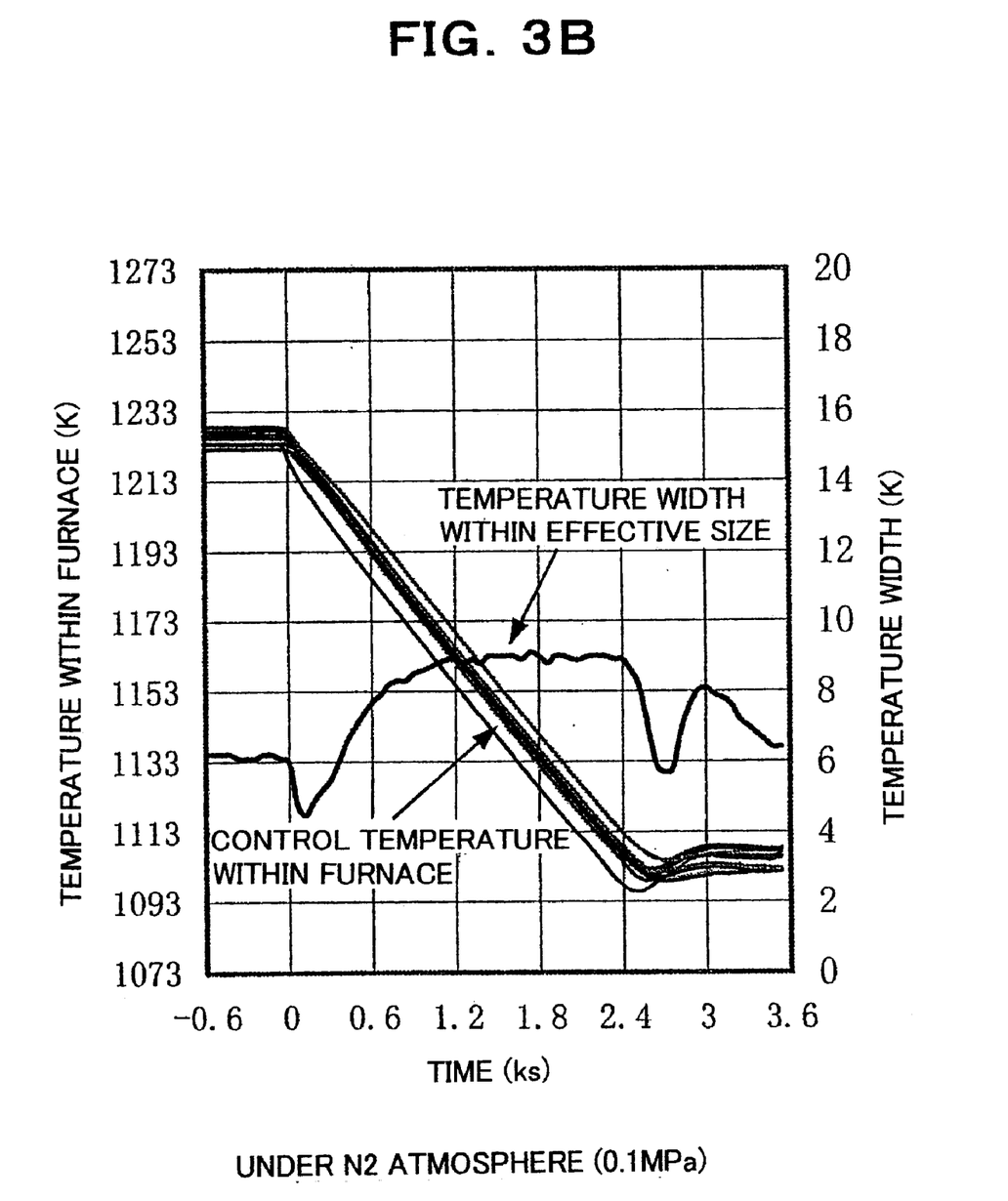
FIG. 3B is a graph showing properties of the vacuum heat treatment furnace shown in FIG. 1 when the temperature is decreased in an atmosphere of $N_2$ gas.

Under N2 gas atmosphere (0.1 MPa) . . . maximum temperature width 9 K, time reaching the average temperature 1103 K within the subject to be treated 2.8 Ks (shown in FIG. 3B)

As mentioned above, in the case of circulating by convection the N2 gas atmosphere, it is possible to make the temperature difference within the subject to be treated smaller and more effectively conduct the heat, in comparison with the vacuum, as shown in Tables 1 and 2.

TABLE 1

TEMPERATURE INCREASING PROPERTY

|  | VACUUM (2 Pa) | N2 GAS ATMOSPHERE (0.1 MPa) | RATE OF REDUCTION |
| --- | --- | --- | --- |
| MAXIMUM TEMPERATURE WIDTH | 298 K | 192 K | 36% |

TABLE 1-continued

TEMPERATURE INCREASING PROPERTY

|  | VACUUM (2 Pa) | N2 GAS ATMOSPHERE (0.1 MPa) | RATE OF REDUCTION |
| --- | --- | --- | --- |
| TEMPERATURE INCREASING TIME | 3.4 Ks | 2.0 Ks | 41% |

TABLE 2

TEMPERATURE REDUCING PROPERTY

|  | VACUUM (0.4 Pa) | N2 GAS ATMOSPHERE (0.1 MPa) | RATE OF REDUCTION |
| --- | --- | --- | --- |
| MAXIMUM TEMPERATURE WIDTH | 9 K | 9 K | 0% |
| TEMPERATURE REDUCING TIME | 3.7 Ks | 2.8 Ks | 24% |

(Embodiment 3)

Figure 4A:
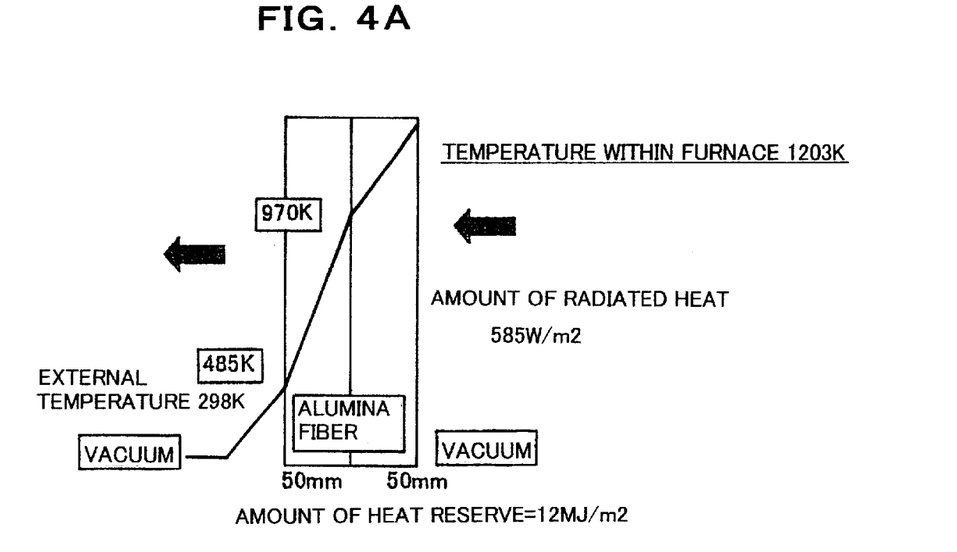
FIG. 4A is a view for explaining properties of the heat insulating layer shown in FIG. 1.
Figure 4B:
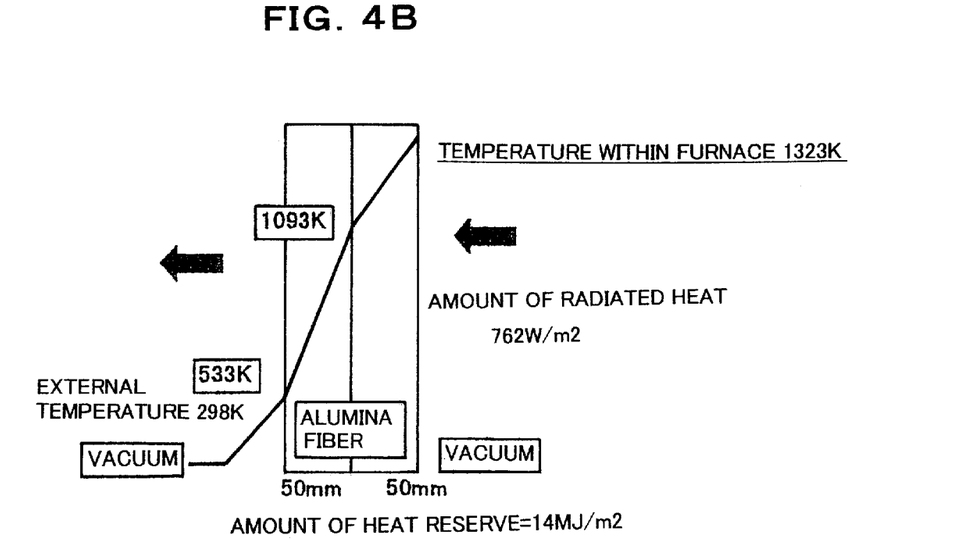
FIG. 4B is a view for explaining properties of the heat insulating layer shown in FIG. 1.

A performance property of the heat insulating layer in the vacuum heat treatment furnace in accordance with the present invention is measured. FIGS. 4A and 4B show a heat insulating material temperature, an amount of heat radiation and an amount of heat reserve at a time when the temperature within the furnace is 1203 K and 1323 K.

(Comparative Embodiment)

In the vacuum heat treatment furnace in accordance with the present invention, the steel part (the weight of the subject to be treated is 85 kg by the gross) is carburized under 1.7 KPa with using a hydrocarbon gas ($C_3H_8$) and an oxidizing gas ($CO_2$). As a result, the same results of carburizing treatment as those of the gas carburizing which has been carried out under the atmospheric pressure can be obtained. Accordingly, the heat insulating properties and the thermal energies in both cases are compared by computing a carburizing and quenching treatment for obtaining an effective quench-hardened layer depth 0.8 mm in a weight of the subject to be treated by the gross 550 kg on the basis of the data obtained by the conventional gas carburizing furnace (TKM-80 manufactured by DOWA KOGYO CO., LTD.) and the vacuum heat treatment furnace in accordance with the present invention.

Figure 5A:
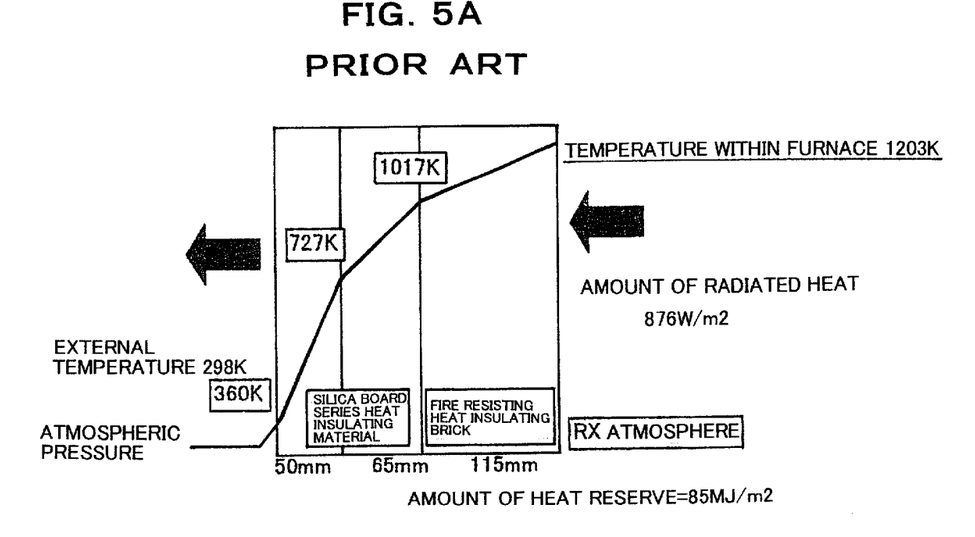
FIG. 5A is a view for explaining properties of a heat insulating layer of a conventional gas carburizing furnace.
Figure 5B:
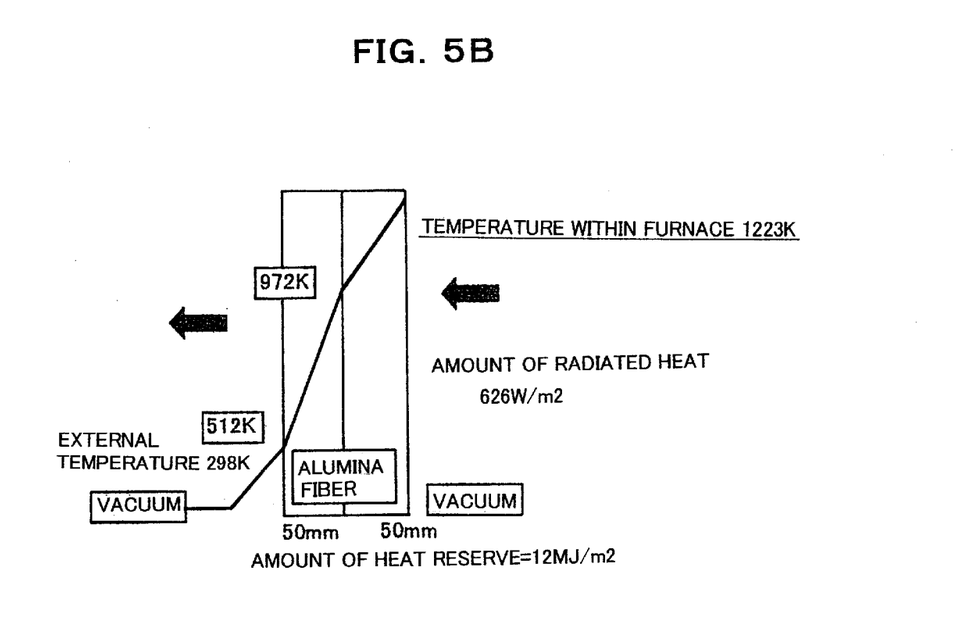
FIG. 5B is a view for explaining properties of the heat insulating layer shown in FIG. 1.
Figure 6A:
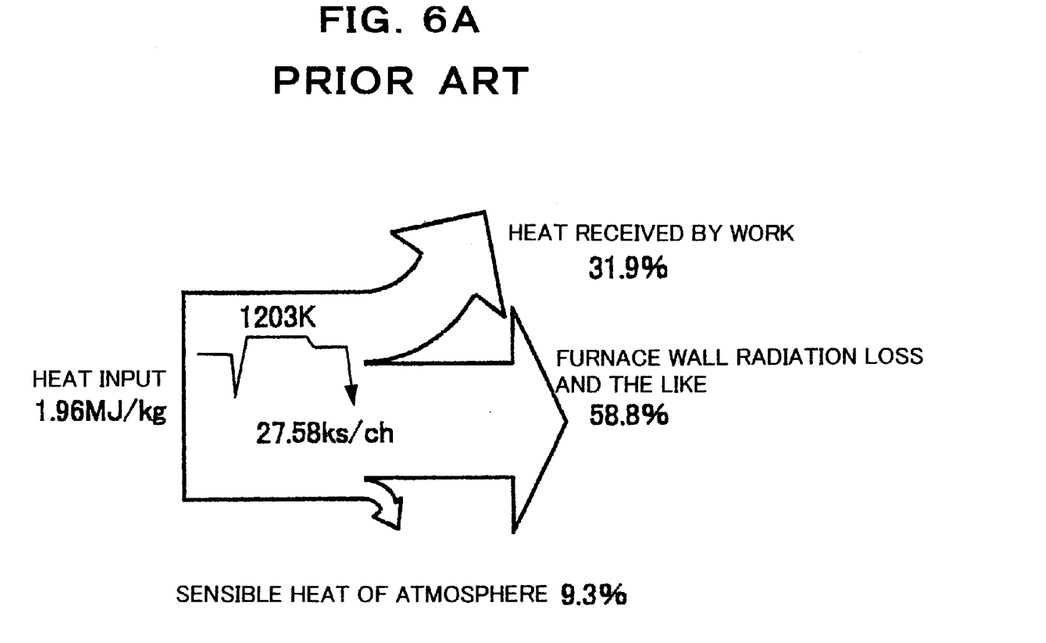
FIG. 6A is a view showing a settlement of thermal energies of a conventional gas carburizing furnace.
Figure 6B:
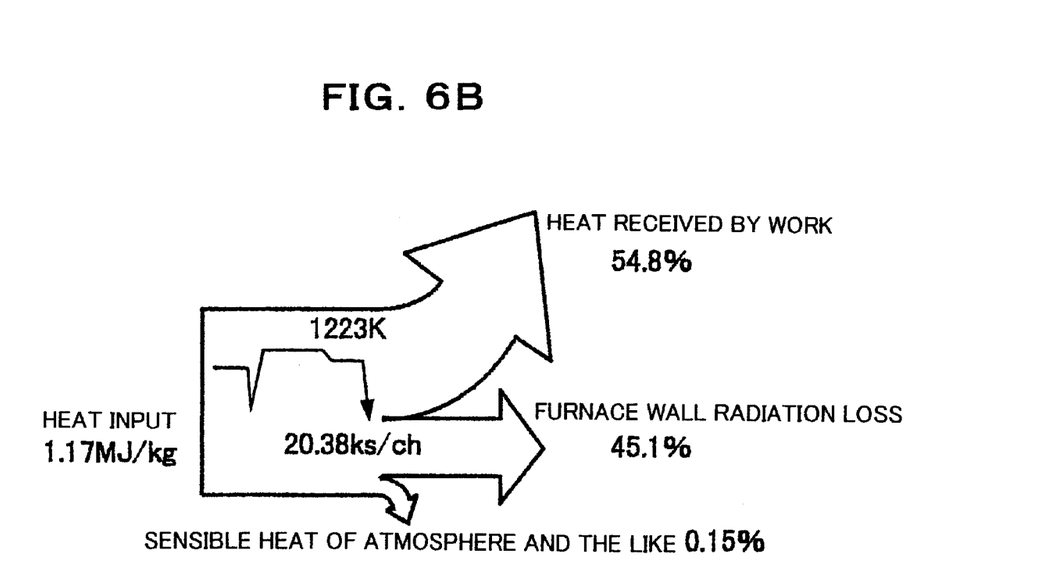
FIG. 6B is a view showing a settlement of thermal energies of the vacuum heat treatment furnace shown in FIG. 1.

As a result of comparing the performance property of the heat insulating layer, it is confirmed that the amount of heat radiation is reduced at 28% and the amount of heat reserve is reduced at 86% as shown in FIGS. 5A and 5B. In the same manner, as a result of comparing the thermal energies, it is possible to reduce the thermal energy at 40% required for obtaining the carburized and quenched product having the same quality due to the reduction of the amount of heat radiation and an improvement of the heat efficiency with respect to the treated product, as shown in FIGS. 6A and 6B.

As described above, in accordance with the present invention, since the iron material and the material which is deteriorated due to the carburizing are not used for the furnace constituting member, the furnace structure is made such as to be easily replaced at a time of the damage and the breakage, and the furnace structure is made such as to restrict the amount of heat reserve to be low while improving the heat insulating material property while water cooling the furnace wall in view of the working environment so as to reduce the amount of heat radiation, and make the heat conducting efficiency with respect to the subject to be treated at a time of increasing and reducing the temperature high, there can be obtained a great advantage that the conventional disadvantage can be further solved.

Figure 7:
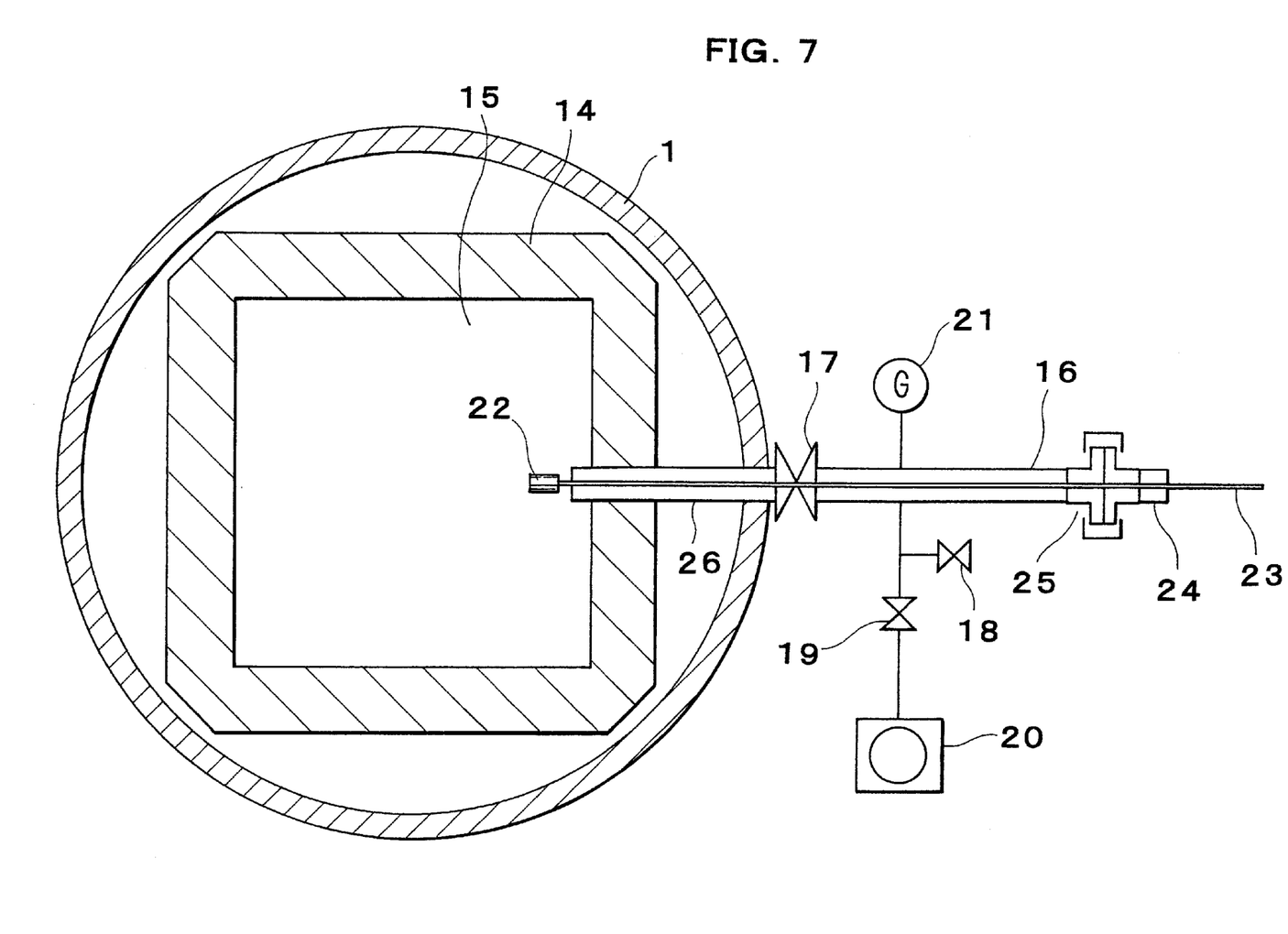
FIG. 7 is a view for explaining an apparatus for measuring a carbon concentration.

Further, FIG. 7 shows an apparatus for measuring a carbon concentration in an atmosphere having a reduced pressure according to the present invention. In FIG. 7, reference numeral 14 denotes a heat insulating layer provided in an inner side of the furnace shell 1, and reference numeral 15 denotes a treating chamber surrounded by the heat insulating layer 14. In accordance with the present invention, a port or tube 16 for inserting a carbon concentration measuring body is provided so as to extend within the treating chamber 15 from an external portion of the furnace shell 1, and the port 16 is provided with a gate valve 17 for isolating the external portion of the furnace shell 1 with an internal portion of the treating chamber 15, a leak valve 18 for returning the internal portion of the port 16 to the atmospheric pressure, a discharge valve 19 required for exhausting the internal portion of the port 16, a vacuum pump 20 and an apparatus 21 with a vacuum meter.

Further, a carbon concentration measuring steel wire 22 is received in a front end of a holding rod 23, a flange 24 having a vacuum seal capable of adjusting a fastening force against the holding rod 23 is mounted to an insertion port flange 25, and the interior portion of the insertion port 16 is exhaust while opening the exhaust valve 19 by means of the vacuum pump 20. After confirming by the vacuum meter that the interior portion of the port 16 is sufficiently exhausted, the treating chamber 15 is communicated with the interior portion of the port 16 by closing the exhaust valve 19 and opening the gate valve 17. After the front end of the holding rod 23 is inserted within the treating chamber 15 by loosening the vacuum seal capable of adjusting the fastening force and guiding the holding rod 23 by the port 16, the vacuum seal is closed so that the holding rod 23 is not drawn further into the treating chamber 15. After reacting the carbon concentration measuring steel wire 22 with the atmosphere within the treating chamber 15 for a predetermined time, the vacuum seal is loosened so as to draw out the front end of the holding rod 23 in which the carbon concentration measuring steel wire 22 is received to a space portion 26 between the furnace shell 1 and the heat insulating layer 14, thereby gradually cooling. After a predetermined time, for example, five minutes have passed, the front end of the holding rod 23 is drawn out to an outer side of the gate valve 17, the gate valve 17 is closed, the exhaust valve 19 is opened, the interior portion of the port 16 is exhausted by the vacuum pump 20, and the carbon concentration measuring steel wire 22 received in the front end of the holding rod 23 is cooled to a room temperature. After cooling, the interior portion of the port 16 is returned to the atmospheric pressure by closing the exhaust valve 19 and opening the leak valve 18, the carbon concentration measuring steel wire 22 received in the front end of the holding rod 23 is taken out by detaching the flange 24 from the flange 25, and an amount of carbon is measured by connecting the steel wire 22 to a connection terminal of an electric resistance measuring device for measuring an electric resistance value of the carbon concentration measuring steel wire 22.

(Embodiment 4)

The carbon concentration of the atmosphere within the furnace under the reduced pressure is measured by the apparatus shown in FIG. 7.

Treating condition: the carbon concentration of the atmosphere within the furnace is measured by changing the carbon concentration of the atmosphere within the furnace under respective conditions comprising a temperature within furnace 1223 K, pressures 100 Kpa, 53 Kpa and 27 Kpa by means of the carbon concentration measuring steel wire, and compared with results obtained by burning and analyzing the steel wire after being measured. As the electric resistance measuring device, a carbon potential meter manufactured by DOWA KOGYO CO., LTD. is employed. As a result, Table 3 is obtained.

TABLE 3

As is apparent from Table 3, it is known that the carbon concentration on the basis of the resistance value measurement in accordance with the present invention substantially coincides with the carbon concentration on the basis of the burning and analyzing. In this case, in accordance with the present invention, a steel foil for measuring the carbon concentration may be used in place of the carbon concentration measuring steel wire 22.

Further, in accordance with the other embodiment of the present invention, in the case of carburizing the subject to be treated within the reduced pressure treating chamber, for example, a steel rod is inserted as a test piece within the treating chamber before the carburizing is started, the steel rod is drawn out from the treating chamber after a predetermined time has passed from the start of the carburizing, for example, at fifteen minutes before a predetermined carburizing is finished. A structure of the steel rod is observed after being gradually cooled, and a carbon concentration of the atmosphere within the treating chamber, a carbon concentration of the steel rod with respect of the insertion time mentioned above, a carburizing motion such as a depth of carburizing or the like and a history are determined on the basis of the results.

In accordance with the structure mentioned above, it is possible to confirm whether or not an expected carburizing quality is obtained for the subject to be treated within the treating chamber, the carburizing treatment is finished at a time when the quality is obtained, and the subject to be treated can be moved forward to a diffusion treating step corresponding to the next step.

As mentioned above, in accordance with this embodiment of the present invention, it is possible to employ the conventional steel wire method of directly measuring the carbon concentration within the heat treatment furnace as the method of measuring the carbon concentration of the atmosphere within the furnace under the reduced pressure in the same manner, so that there can be obtained a great advantage that it is possible to easily measure the carbon concentration of the atmosphere within the furnace in the middle of the carburizing treatment which has not been conventionally carried out under the reduced pressure treatment.

While the invention has been particularly shown and described with reference to the preferred embodiments thereof, it will be understood by those skilled in the art that various changes in form and details may be made therein without departing from the spirit and scope of the invention as defined by the appended claims.

What is claimed is:

1. A vacuum heat treatment furnace comprising a furnace shell, a casing arranged in an inner side of the furnace shell, a thin plate-like alumina series ceramic material arranged in an inside of the casing, a heat insulating layer inserted between the thin plate like alumina series ceramic material and the casing, and a heater arranged in a heating room surrounded by the heat insulating layer, wherein the heat insulating layer includes a thick plate-like alumina-silica series ceramic fiber blanket and a high alumina-silica series ceramic fiber blanket.

2. The vacuum heat treatment furnace as claimed in claim 1, wherein the furnace shell is of water cooled type.

3. The vacuum heat treatment furnace as claimed in claim 1, further comprising a fan formed of a high strength carbon fiber for circulating by convection gas atmosphere, arranged in the heating room surrounded by the heat insulating layer.

4. The vacuum heat treatment furnace as claimed in claim 1, further comprising a roller for transferring a subject to be treated, and a tray guide which is easy to replace and prevents the surface of the roller from being damaged, both of the roller and the tray guide being arranged in the heating room surrounded by the heat insulating layer.

5. The vacuum heat treatment furnace as claimed in claim 4, wherein the roller is made of a high strength carbon fiber.

6. The vacuum heat treatment furnace as claimed in claim 4, wherein the tray guide is made of a high strength carbon fiber, high strength carbon fiber impregnated with Si, or ceramic.

7. The vacuum heat treatment furnace as claimed in claim 1, further comprising a work position detecting device arranged in the heating room surrounded by the heat insulating layer.

8. The vacuum heat treatment furnace as claimed in claim 7, wherein the work position detecting device is made of a high strength carbon fiber.

* * * * *